(12) United States Patent
Herlihy et al.

(10) Patent No.: US 8,022,111 B2
(45) Date of Patent: Sep. 20, 2011

(54) PIPERAZINO SENSITISERS

(75) Inventors: Shaun Lawrence Herlihy, Chatham (GB); Brian Rowatt, Maidstone (GB)

(73) Assignee: Sun Chemical Corporation, Parsippany, NJ (US)

( * ) Notice: Subject to any disclaimer, the term of this patent is extended or adjusted under 35 U.S.C. 154(b) by 1069 days.

(21) Appl. No.: 10/587,588

(22) PCT Filed: Jan. 28, 2005

(86) PCT No.: PCT/US2005/003505
§ 371 (c)(1),
(2), (4) Date: May 16, 2007

(87) PCT Pub. No.: WO2005/073208
PCT Pub. Date: Aug. 11, 2005

(65) Prior Publication Data
US 2007/0244210 A1     Oct. 18, 2007

(30) Foreign Application Priority Data
Jan. 29, 2004     (GB) .................................. 0401959.2

(51) Int. Cl.
*C08F 2/46* (2006.01)
*C07D 403/00* (2006.01)
*C09D 11/00* (2006.01)
*G03F 7/00* (2006.01)

(52) U.S. Cl. ............... 522/8; 522/16; 523/160; 544/358; 544/395; 544/399; 544/403; 427/510; 430/281.1

(58) Field of Classification Search .................. 544/358, 544/395, 399, 403; 522/8, 16; 523/160; 427/510; 430/281.1
See application file for complete search history.

(56) References Cited

U.S. PATENT DOCUMENTS
4,147,604 A     4/1979     Kuesters et al.

FOREIGN PATENT DOCUMENTS
EP     0143201 A2     6/1985
JP     6211759 A     8/1994

OTHER PUBLICATIONS

Stefan Spange et al., Solid-state Structures of N-Substituted Michler's Ketones and Their Relation to Solvatochronism, European Journal of Organic Chemistry, 2002, pp. 4159-4168.

*Primary Examiner* — Paul V. Ward
(74) *Attorney, Agent, or Firm* — McKenna Long & Aldridge, LLP.

(57) ABSTRACT

Compounds of formula (I) [in which: A and B are terminal groups; $R^1$ represents a group of formula (II) or (III); $R^2$ is alkyl or aryl; Z is a group $-(CHR^3)_n$-, where $R^3$ is hydrogen, hydroxy or alkyl, and n is a number from 0 to 6; Y is carbonyl or a group $-CH_2-$; Q represents a residue of a dihydroxy compound; and x is a number from 1 to 100] are useful sensitisers for use with Type II photoinitiators in the formulation of printing inks and other energy curable coatings.

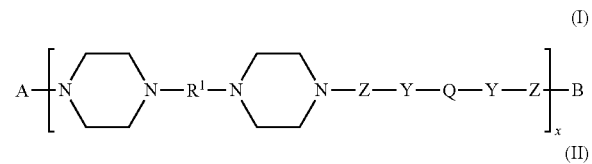

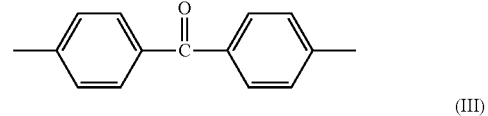

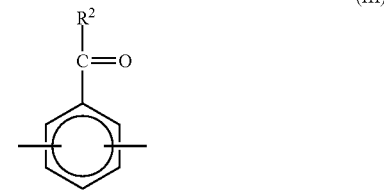

23 Claims, 1 Drawing Sheet

PIPERAZINO SENSITISERS

CROSS REFERENCE TO RELATED APPLICATIONS

Figure 1:
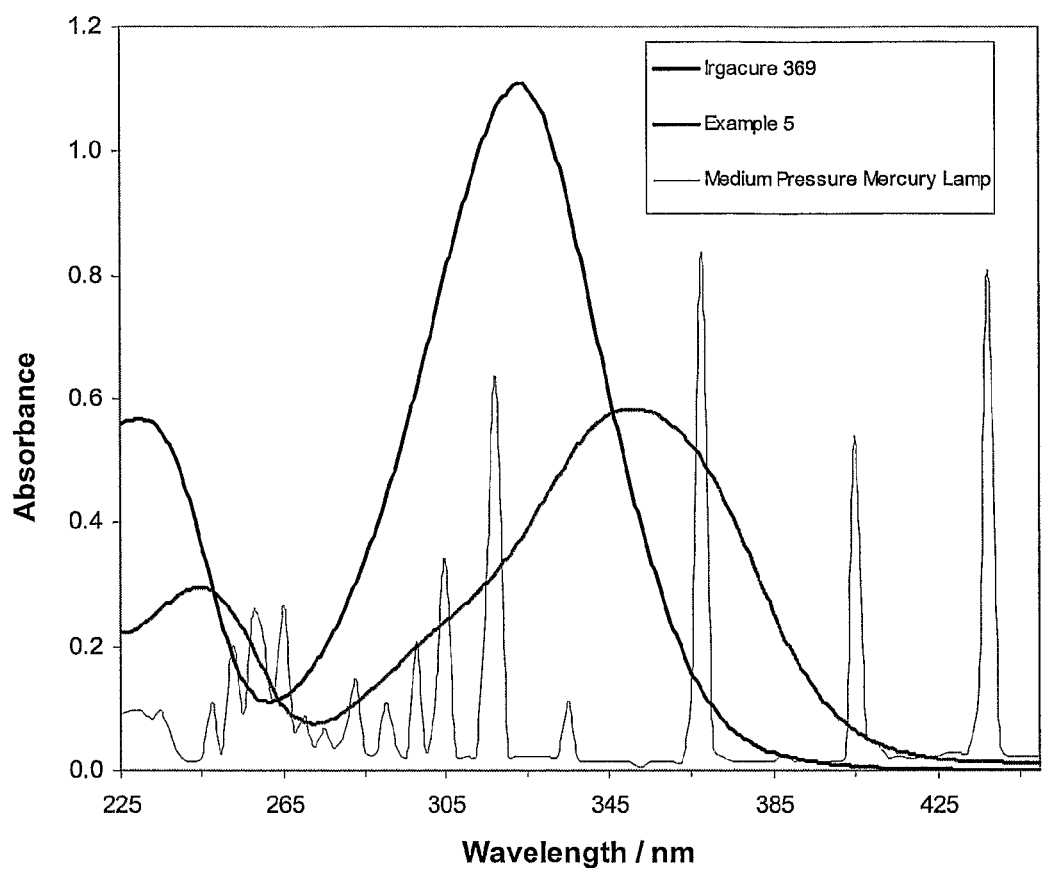

This application is the United States national stage filing of corresponding international application number PCT/US2005/003505 filed on Jan. 28, 2005, which claims priority to and benefit of Great Britain application number 0401959.2, filed Jan. 29, 2004 each of which is hereby incorporated herein by reference.

The present invention relates to a series of new piperazine-based sensitisers for use in radiation curing, for example in the radiation curing of coating compositions such as printing inks or varnishes.

Photocurable compositions are cured by exposure to radiation, usually ultraviolet radiation, and include for example, lacquers which may be applied to wood, metal or similar substrates by suitable techniques such as roll coating or curtain coating. They may also be formulated as inks, for example to be applied by techniques such as letterpress, offset lithography, rotogravure printing, silk screen printing, flexographic or ink jet printing. Printing, depending on the particular printing technique, is applicable to a wide range of substrates which include paper, board, glass, plastics materials or metals.

Such compositions will contain the monomer or oligomer to be polymerised, together with a photoinitiator, whose function is to absorb the radiation, and form an excited state which can then initiate polymerisation. In addition, there may be a sensitiser, whose function is to enhance and/or broaden the absorption spectrum of the initiator. Where, as is common, the composition is to be used in liquid form, there may also be a solvent/viscosity modifier, which is preferably also polymerisable. However, it is normally preferred to avoid any such additive, if possible, as it may modify the properties of the final polymerised coating in unpredictable or undesirable ways.

Michler's ketone is the most well-known sensitiser for radiation curing. Although it can function as a photoinitiator in its own right, Michler's ketone is not particularly efficient as it has a significant charge transfer character to its lowest lying triplet state. This makes hydrogen abstraction from donor molecules unfavourable due to the high electron density on the carbonyl oxygen. However, a combination of benzophenone and Michler's ketone acts as a synergistic combination due to the formation of an excited state complex which can be populated by excitation of either molecule.

We have now surprisingly found a series of piperazine compounds which can be used with Type II photoinitiators to provide extremely efficient radiation cure.

Thus, the present invention consists in compounds of formula (I):

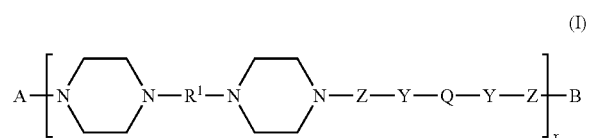

in which:
A and B are terminal groups;
$R^1$ represents a group of formula (II) or (III):

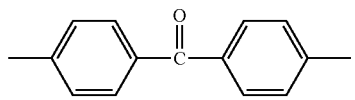

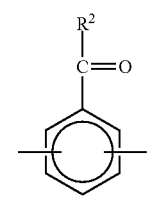

$R^2$ represents a $C_1$-$C_6$ alkyl group, an aryl group or a substituted aryl group having one or more $C_1$-$C_6$ alkyl, $C_1$-$C_6$ alkoxy or phenyl substituents;
Z represents a group of formula —$(CHR^3)_n$—, where $R^3$ represents a hydrogen atom, a hydroxy group or a $C_1$-$C_4$ alkyl group, and n is a number from 0 to 6;
Y represents a carbonyl group or a group of formula —$CH_2$—;
Q represents a residue of a dihydroxy compound; and
x is a number from 1 to 100.

The present invention also provides an energy-curable composition comprising: (a) a polymerisable monomer, prepolymer or oligomer; (b) a photoinitiator and, optionally, a synergist, and (c) a sensitiser which is a compound of formula (I).

The invention still further provides a process for preparing a cured polymeric composition by exposing a composition according to the present invention to actinic radiation, preferably ultraviolet radiation.

The nature of the terminal groups represented in the above formula by A and B is not critical to the present invention, although, of course, they may have an influence on the properties of the compound of formula (I). For convenience of preparation, they will normally be derived from the compound(s) used to prepare the remainder of the compound of formula (I), rather than selected especially and added by a separate reaction. Preferably, A represents a hydrogen atom, or a group of formula:

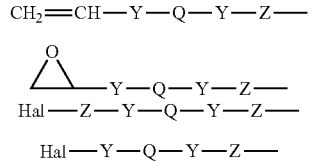

where Y, Q and Z are as defined above and Hal represents a halogen atom, preferably a chlorine or bromine atom. More preferably A is one of the aforementioned groups.

Preferably, B represents a halogen atom or a group of formula:

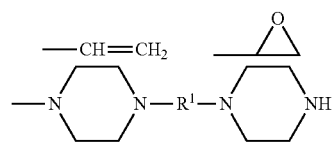

in which $R^1$ is as defined in claim 1 and Hal represents a halogen atom, preferably a chlorine or bromine atom. More preferably B represents a halogen atom or a group of formula:

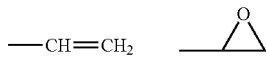

in which Hal represents a halogen atom.

In the compounds of the present invention, where $R^1$ represents a group of formula (III) and $R^2$ represents an alkyl group, this may be a straight or branched chain group and may have from 1 to 6 carbon atoms. Examples of such groups include the methyl, ethyl, propyl, isopropyl, butyl, isobutyl, sec-butyl, t-butyl, pentyl, isopentyl, neopentyl, hexyl and isohexyl groups, of which those groups having from 1 to 4 carbon atoms are preferred, more preferably the methyl or ethyl groups.

Where $R^1$ represents a group of formula (III) and $R^2$ represents an aryl group, this may be unsubstituted or it may be substituted with one or more of the substituents below. The aryl group may have one or more rings, and, if more than one, the rings may be fused. The aryl group preferably has from 6 to 10 carbon atoms, and examples include the phenyl, 1-naphthyl, 2-naphthyl and indenyl groups, of which the phenyl group is preferred.

Where the aryl group represented by $R^2$ is substituted, there is no restriction on the number of substituents, except such as may be imposed by the number of substitutable positions, and possibly by steric constraints. In general, there will normally be from 1 to 5, more commonly from 1 to 3 substituents. Examples of such substituents include $C_1$-$C_6$ alkyl groups (as defined and exemplified above in relation to the groups which may be represented by $R^1$), $C_1$-$C_6$ alkoxy groups and phenyl groups. However, the aryl group is preferably unsubstituted and the preferred aryl group is the unsubstituted phenyl group.

Where the substituent is an alkoxy group, this may be a straight or branched chain group and may have from 1 to 6 carbon atoms. Examples of such groups include the methoxy, ethoxy, propoxy, isopropoxy, butoxy, isobutoxy, sec-butoxy, t-butoxy, pentyloxy, isopentyloxy, neopentyloxy, hexyloxy and isohexyloxy groups, of which those groups having from 1 to 4 carbon atoms are preferred, more preferably the methoxy or ethoxy groups.

Where Z represents a group of formula —$(CHR^3)_n$—, and $R^3$ represents a $C_1$-$C_4$ alkyl group, the alkyl group may be a methyl, ethyl, propyl, isopropyl, butyl, isobutyl, sec-butyl or t-butyl group, preferably a methyl group. n is a number from 0 to 6, and is preferably from 0 to 3.

In one embodiment of the present invention, Q represents a group of formula -D-Q'-D-, where D represents a group of formula —[O(CHR$^4$—(CHR$^5$)$_a$]$_y$—, —[O(CH$_2$)$_b$CO]$_y$— or —[O(CH$_2$)$_b$CO]$_{(y-1)}$—[O(CHR$^4$CHR$^5$)$_a$]—; and where:

$R^4$ and $R^5$ are the same or different and each represents a hydrogen atom or a $C_1$-$C_4$ alkyl group;
a is a number from 1 to 2;
b is a number from 4 to 5; and
y is a number from 1 to 10; and
Q' represents a residue of a dihydroxy compound.

In the compounds of this embodiment of the present invention, we prefer that D should represent a group of formula —[O(CHR$^4$CHR$^5$)$_a$]$_y$— where a is a number from 1 to 2, y is as defined above, preferably a number from 3 to 10, and $R^4$ and $R^5$ are the same or different and each represents a hydrogen atom or a $C_1$-$C_4$ alkyl group. More preferably D represents a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is as defined above, preferably a number from 3 to 10, or a group of formula —[O(CH$_2$)$_b$CO]$_y$— or —[O(CH$_2$)$_b$CO]$_{(y-1)}$—[O(CHR$^4$CHR$^5$)$_a$]—, where b is a number from 4 to 5 and $R^4$, $R^5$ and y are as defined above, y preferably being a number from 3 to 10. Still more preferably, y is a number from 3 to 6.

In general, in the compounds of the present invention, y is preferably a number from 3 to 10, more preferably from 3 to 6

Where $R^4$ and/or $R^5$ represent an alkyl group having from 1 to 4 carbon atoms, these may be any of those alkyl groups exemplified in relation to $R^3$.

The compounds of this embodiment of the present invention are preferably of a generally polymeric nature. The polymeric nature may be provided by either the group represented by Q' or the group represented by D or by both.

The polymeric dihydroxy residue of formula -D-Q'-D-, which forms the core of the compounds of the present invention has a major influence on the behaviour of the compounds. In accordance with the present invention, it is preferred that it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula -D-Q'-D-, should not have too high a molecular weight, and prefer that the residue of formula -D-Q'-D- should have a molecular weight no greater than 2000, preferably no greater than 1200, still more preferably no greater than 1000, and most preferably no greater than 800.

We particularly prefer that Q' is a residue of a $C_2$-$C_6$ alkylene glycol or of a polyalkylene glycol, in which the alkylene part has from 2 to 6 carbon atoms. More preferably, Q' is a residue of ethylene glycol, propylene glycol, butylene glycol, glycerol, 2,2-propanediol, neopentyl glycol, polyethylene glycol, polypropylene glycol or polybutylene glycol.

It will be appreciated that, when the compounds of the present invention are analysed, the numbers a, b, y and x in the above formulae need not be integral, and, indeed, it is unlikely that they will be integral, since the compounds of the present invention may be mixtures of several compounds in which the numbers a, b, y and x differ. In accordance with the present invention, provided that the average value of each, of these numbers is as defined above, this will be satisfactory. Of course, for each individual molecule of the compounds of the present invention, a, b, y and x will be integral, and it might be possible to separate out such individual compounds, but, in practice, mixtures of these compounds are used.

In another preferred embodiment of the present invention, Q is a residue of a $C_2$-$C_6$ polyalkylene glycol, in which the alkylene part has from 2 to 6 carbon atoms. Alternatively, Q may be a bis($C_1$-$C_6$ hydroxyalkyl)ether, where the two hydroxyalkyl parts may be the same as or different from each other, although they are preferably the same, and each may have one or more hydroxy groups. In this embodiment, Q is preferably a residue of ethylene glycol, propylene glycol, butylene glycol, glycerol, 2,2-propanediol, neopentyl glycol, polyethylene glycol, polypropylene glycol or polybutylene glycol.

x may be a number from 1 to 100, more preferably from 1 to 50, still more preferably from 1 to 20 and most preferably from 1 to 10.

The compounds of the present invention may be prepared simply, for example by nucleophilic addition or nucleophilic substitution of a compound of formula (IV):

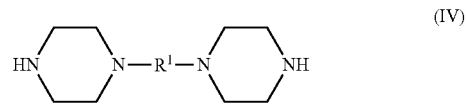

(in which A is as defined above) with an active compound of formula B—Z—Y-Q-Y—Z—B (where Z, Y, Q and B are as defined above). This active compound may, for example, be a compound including a carbon-carbon double bond, an epoxide group, a halo-alkyl ester or a halo-formate group, as illustrated in more detail in the Examples appearing hereafter.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, photoinitiator, amine synergist and the sensitiser of the present invention, but may also include other components well known to those skilled in the art, for example, waxes, flow aids and, in the case of printing inks, a pigment.

The compounds of the present invention will sensitise a wide variety of Type II initiators, generally, benzophenone derivative photoinitiators, in current use, and the exact nature of the photoinitiator used in the composition of the present invention is, therefore, not particularly critical to the invention, although its choice may well have an important effect on the properties of the cured composition or the ease or extent of cure, as is well known in the art. Examples of such photoinitiators include: benzophenone, 4-methylbenzophenone, 4-phenylbenzophenone and benzophenone 2-methyl ester.

A wide variety of monomers and prepolymers may be subjected to photoinitiation with these photoinitiators, and using the compounds of the present invention as sensitisers, and the nature of the monomers and prepolymers is not critical to the present invention.

The radiation-curable monomer or oligomer is preferably an ethylenically unsaturated compound, for example an acrylate or methacrylate. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetraacrylate, di-pentaerythritol pentaacrylate, polyether acrylates, such as ethoxylated trimethylol propane triacrylate, glycerol propoxylate triacrylate, ethoxylated pentaerythritol tetraacrylate, epoxy acrylates such as dianol diacrylate (=the diacrylate of 2,2-bis[4-(2-hydroxyethoxy)phenyl]propane, Ebecryl 150 from UCB), glycol diacrylates such as tripropylene glycol diacrylate and alkyl acrylates and methacrylates (such as hexanediol diacrylate, isobornyl acrylate, octadecyl acrylate, lauryl acrylate, stearyl acrylate and isodecyl acrylate, and the corresponding methacrylates).

Also, the compositions of the present invention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used, in flexographic printing applications, may contain both amine types.

Although the compositions of the present invention preferably contain a synergist, such as an aminoacrylate, as is well known in the art, the use of products of this invention in a well formulated system may also allow the level of standard amine synergists to be reduced or allow them to be eliminated altogether.

The amounts of the radiation-curable monomer or oligomer, photoinitiator, synergist and optional colorant will vary according to the type of varnish or ink, the particular equipment to be used to apply it and the application. However, typically, the amount of photoinitiator plus amine synergist is from 1% to 15-20% by weight of the total composition.

The compounds of formula (I) are especially suited for varnishes and inks, especially printing inks, including lithographic inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference. Since the compounds of the present invention cause yellowing, they may only be used successfully in varnishes if this is not of importance.

Additives which may be used in conjunction with the principal components of the coating formulations of the present invention include stabilisers, plasticisers, pigments, waxes, slip aids, levelling aids, adhesion promoters, surfactants and fillers. Also other photoinitiators, such as thioxanthone (and derivatives), benzophenone (and derivatives), hydroxyalkylphenones, aminoalkylphenones and anthraquinone (and derivatives) may be included.

The compounds of the present invention may be included as sensitisers in coating formulations such are well known in the art, and the precise composition of such formulations will vary depending upon the other components and the intended use, as is well known. However, a typical formulation for an ink coatable by flexography might be:

| | |
|---|---|
| Pigment | 8-20% |
| Photoinitiator + synergist | 4-10% |
| Monomer/prepolymer/oligomers | 30-90% |
| Additives | 0-10% |
| Sensitiser | 1-5%, | although inks may have compositions outside these ranges as is well known in the art.

The invention is further illustrated by the following non-limiting Examples.

EXAMPLE 1

Preparation of 4,4'-dipiperazinobenzophenone

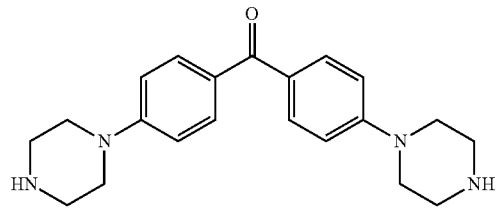

5.0 g of 4,4'-difluorobenzophenone (0.0229 moles), 3.94 g of piperazine (0.0458 moles), 6.60 g of potassium carbonate powder (0.0478 moles) and 50 ml dry DMSO (dimethyl sulphoxide) were mixed in a three necked flask equipped with a stirrer, nitrogen inlet, condenser, calcium chloride drying tube/nitrogen outlet and a temperature probe. The mixture was heated to reflux for a total of 12 hours (~190° C.) under a constant flow of nitrogen gas. The mixture was then cooled to room temperature and filtered to remove the inorganics. A further 75 ml of DMSO was used to wash out the reaction flask. The DMSO solution was then added to 100 g of water. The mixture obtained was extracted with 3×75 ml of dichloromethane. The dichloromethane layers were combined and were washed with 100 ml of saturated sodium chloride solution. The dichloromethane layer was then dried using anhydrous magnesium sulphate. The magnesium sulphate was removed by filtration and the dichloromethane was then removed on a rotary evaporator to yield the crude product. 30 ml of water was added to the crude product and the mixture was then filtered to recover the product. The product was washed with a further 100 ml of water and then dried in a vacuum oven at 60° C. for 4 hours.

Product yield 4.64 g (36.63%) of a yellow solid.
The product was analysed by IR, and LCMS.
IR: aryl C—N at 1321 cm$^{-1}$.
MS: M/Z 351 (Mw of cation)

EXAMPLE 2

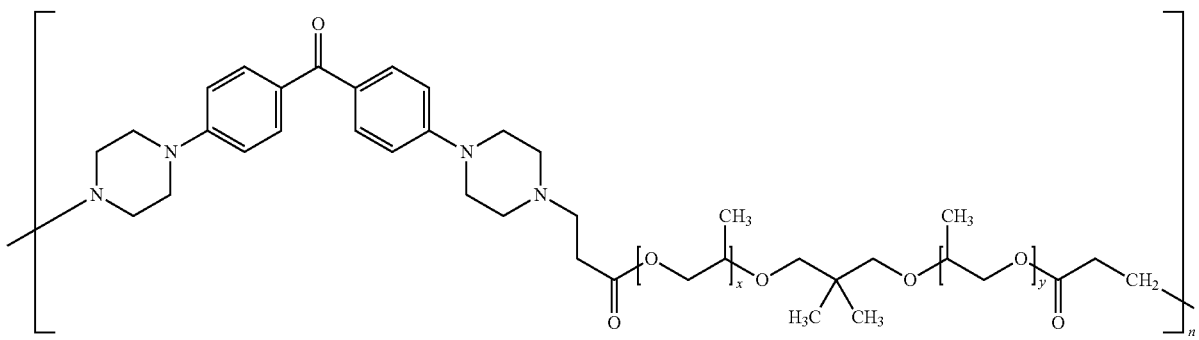

2.84 g Propoxylated neopentyl glycol diacrylate (PN-PGDA, mol. wt. 328) (0.00866 moles), 2.00 g of the product of Example 1 (4,4'-dipiperazinobenzophenone) (0.00571 moles), toluene 30 ml and 0.115 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone, and then the solvent was removed on a rotary evaporator to yield the product.

Product yield 4.95 g of a viscous slightly yellow liquid.
The product was analysed by GPC.
GPC: Mn 5167, Mw 11664.

EXAMPLE 3

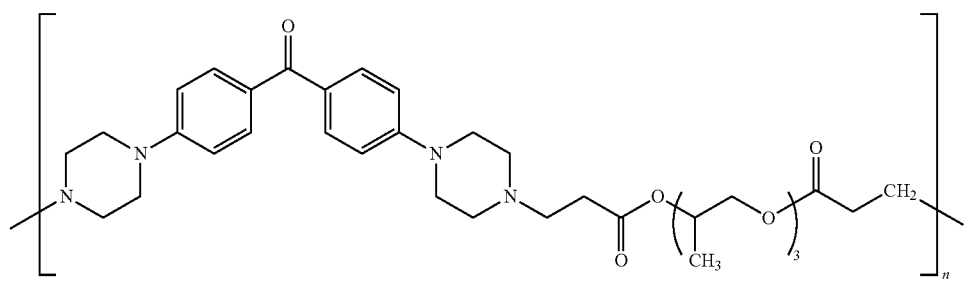

2.60 g tripropylene glycol diacrylate (TPGDA, mol. wt. 300) (0.00866 moles), 1.515 g of the product of Example 1 (4,4'-dipiperazinobenzophenone) (0.00433 moles), toluene 30 ml and 0.115 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 3.77 g (91.6%) of a viscous slightly yellow liquid.

The product was analysed by GPC.
GPC: Mn 3165, Mw 3885

EXAMPLE 4

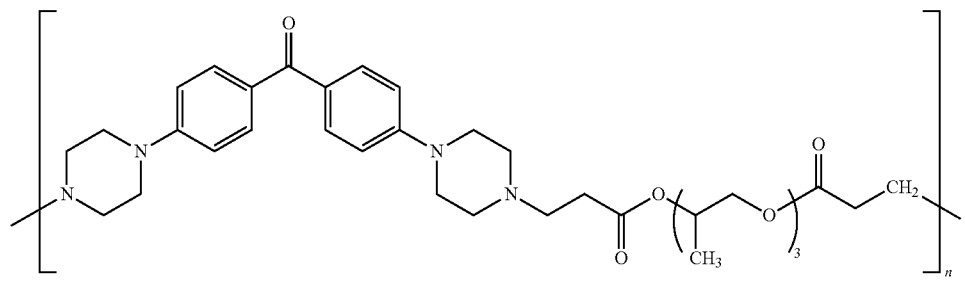

2.275 g tripropylene glycol diacrylate (TPGDA, mol. wt. 300) (0.00758 moles), 1.515 g of the product of Example 1 (0.00433 moles), toluene 30 ml and 0.115 g 1,8-diazabicyclo (5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 2.71 g (71.50%) of a viscous yellow liquid. The product was analysed by GPC.
GPC: Mn 5692, Mw 9932.

EXAMPLE 5

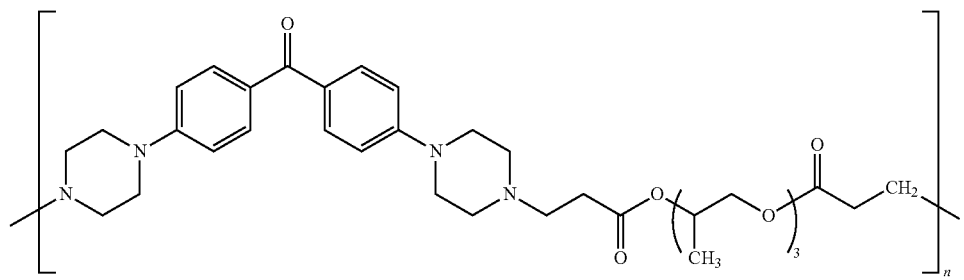

1.95 g tripropylene glycol diacrylate (TPGDA, mol. wt. 300) (0.00649 moles), 1.515 g of the product of Example 1 (0.00433 moles), toluene 30 ml and 0.115 g 1,8-diazabicyclo (5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 3.52 g (100%) of a viscous yellow liquid. The product was analysed by GPC.
GPC: Mn 3230, Mw 4871.

EXAMPLE 6

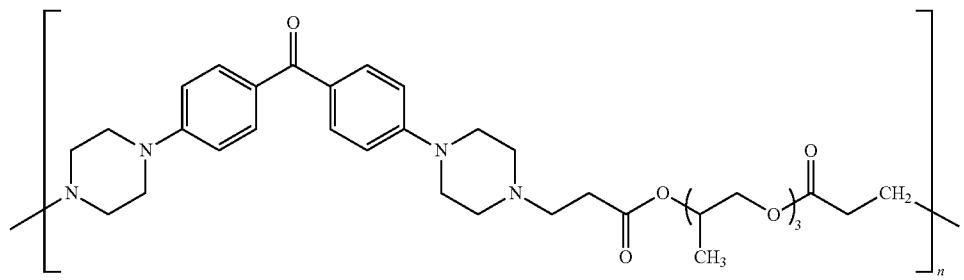

1.625 g tripropylene glycol diacrylate (TPGDA, mol. wt. 300) (0.00541 moles), 1.515 g of the product of Example 1 (0.00433 moles), toluene 30 ml and 0.115 g 1,8-diazabicyclo (5.4.0)undec-7-ene (DBU) (catalyst) were mixed in a two necked round bottomed flask equipped, with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 2.75 g (87.6%) of a viscous yellow liquid. The product was analysed by GPC.
GPC: Mn 4033, Mw 7063.

EXAMPLE 7

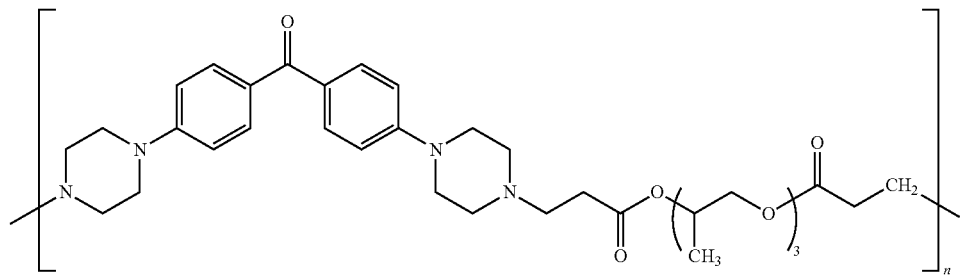

1.365 g tripropylene glycol diacrylate (TPGDA, mol. wt. 300) (0.00455 moles), 1.515 g of the product of Example 1 (0.00433 moles), toluene 30 ml and 0.115 g 1,8-diazabicyclo (5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 2.74 g (95.14%) of a viscous yellow liquid. The product was analysed by GPC.
GPC: Mn 4737, Mw 6764.

EXAMPLE 8

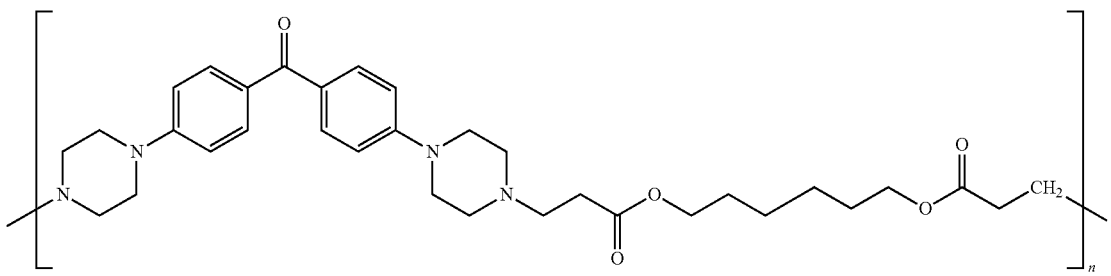

1.47 g hexanediol diacrylate (HDDA, mol. wt. 226) (0.00649 moles), 1.515 g of the product of Example 1 (0.00433 moles), toluene 30 ml and 0.115 g 1,8-diazabicyclo (5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to pew the product.

Product yield 2.09 g (70.02%) of a pasty yellow solid. The product was analysed by GPC.
GPC: Mn 13107, Mw 35067.

EXAMPLE 9

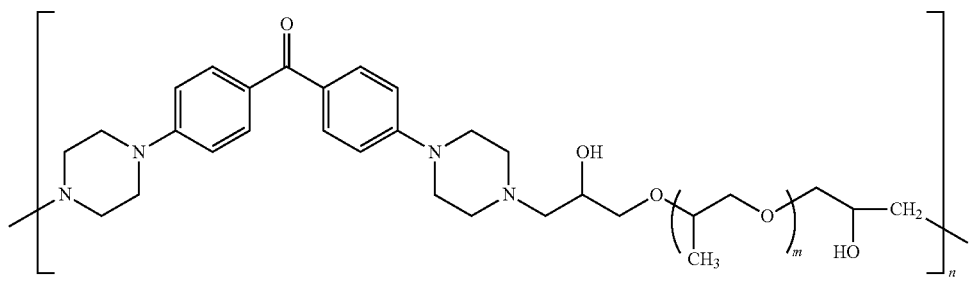

2.47 g polypropylene glycol diglycidyl ether (PPGDGE, mol. wt. 380) (0.00649 moles), 1.515 g of the product of Example 1 (0.00433 moles) and toluene 30 ml were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 2.00 g (50.2%) of a viscous yellow liquid.
The product was analysed by GPC.
GPC: Mn 5706, Mw 7134.

EXAMPLE 10

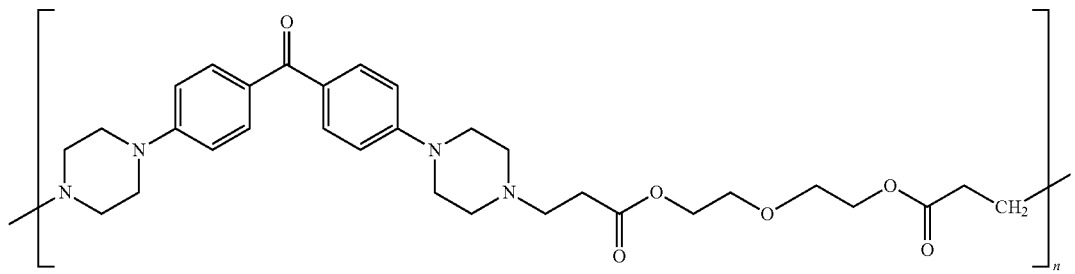

1.39 g diethylene glycol diacrylate (DEGDA, mol. wt. 214.2) (0.00649 moles), 1.515 g of the product of Example 1 (0.00433 moles), toluene 30 ml and 0.115 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4,4'-dipiperazinobenzophenone and then the solvent was removed on a rotary evaporator to yield the product.

Product yield 2.43 g (83.65%) of a viscous yellow liquid.
The product was analysed by GPC.
GPC: Mn 2400, Mw 5140.

EXAMPLE 11

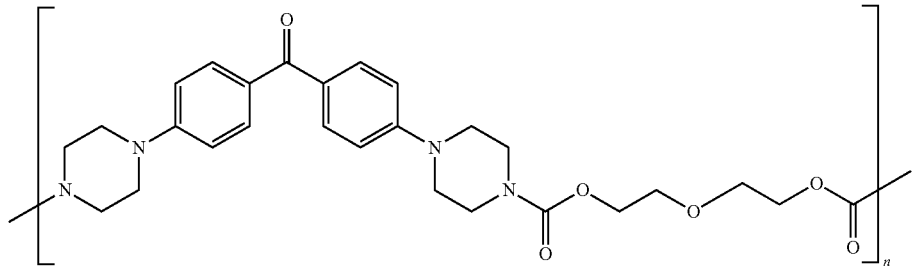

5.0 g of the product of Example 1 (4,4'-dipiperazinobenzophenone, 0.01395 moles), 2.818 g of triethylamine (0.0279 moles) and 50 ml of toluene were mixed in a two necked flask equipped with a stirrer, condenser and a temperature probe. 3.0 g of diethylene glycol chloroformate (0.01395 moles) in 45 ml of toluene were then added slowly ensuring the exotherm was controlled (temperature maximum throughout the addition was 35° C.). After the addition was complete, the mixture was stirred for 4 hours, allowing the mixture to cool to room temperature. The mixture was then filtered to remove the insoluble triethylamine hydrochloride formed during the reaction. The toluene was then removed on a rotary evaporator to yield the product Product yield 2.51 g (36.6%) of a viscous yellow liquid.
The product was analysed by GPC.
GPC: Mn 1201, Mw 1406.

EXAMPLE 12

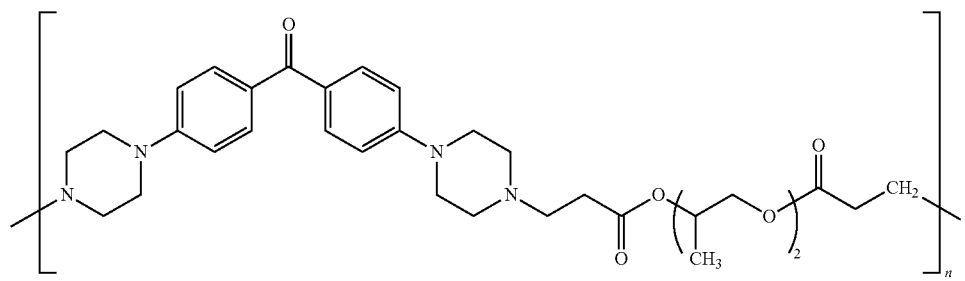

20.0 g dipropylene glycol diacrylate (DPGDA, mol. wt. 242) (0.0826 moles), 16.53 g of the product of Example 1 (0.0472 moles), toluene 130 ml and 1.26 g 1,8-diazabicyclo (5.4.0)undec-7-ene (DBU) (catalyst) were mixed in a two necked round bottomed flask equipped with a stirrer, condenser and temperature probe. The mixture was heated to reflux for a total of 12 hours (over 2 days). The mixture was then cooled and filtered to remove unreacted 4,4'-dipiperazinobenzophenone and then the solvent was removed on a rotary evaporator to yield the product.

Product yield 36.26 g (99.26%) of a viscous yellow liquid.

EXAMPLE 13

Performance Evaluation In Offset Inks

The performance of the new materials was assessed in a black offset ink formulation based on a tri-functional urethane acrylate oligomer. A photoinitiator blend was added as 10% of the overall formulation, this comprised:

| | |
|---|---|
| 25% | Benzophenone 2-methyl ester (MBB) |
| 25% | isopropylthioxanthone (ITX) |
| 30% | 2-ethylhexyl p-dimethylaminobenzoate (EHA) |
| 20% | sensitiser |

In the control formulation, the sensitiser was substituted by EHA giving an overall level of 50% EHA, as would be typical in a normal commercial formulation. The inks were printed onto a carton board substrate (Incada Silk 260 gsm from Iggesund) to a density of approximately 1.8 using an IGT C1 print proofer. These were cured at 100 m/min using a Primarc Maxicure UV rig fitted with a single 300 W/inch medium pressure mercury lamp, operating at full power. The number of passes required to cure was measured using the "thumb twist test" and is shown in Table 1.

TABLE 1

Cure speed of inks containing piperazine derivatives

| Sensitiser | No. passes to cure |
|---|---|
| EHA | 7 |
| Example 3 | 3-4 |
| Example 4 | 4 |
| Example 5 | 4-5 |
| Example 6 | 5 |
| Example 7 | 5 |
| Example 8 | 4 |

TABLE 1-continued

Cure speed of inks containing piperazine derivatives

| Sensitiser | No. passes to cure |
|---|---|
| Example 9 | 5-6 |
| Example 10 | 3 |
| Example 11 | 3-4 |

The results in Table 1. show that, despite an addition level of only 20% (2% in the formulated ink), all the Examples boost the cure speed of the formulation significantly, particularly Example 10.

EXAMPLE 14

UV Spectra of Sensitiser Compounds

The sensitiser compounds of the invention all have strong characteristic UV absorbance chromophores which allows them to compete effectively with pigments for the available light from the curing lamp. This is demonstrated by the spectra in FIG. 1 for the product of Example 5 in comparison with the well known, strongly absorbing and highly effective photoinitiator Irgacure 369. Compared to Irgacure 369, the compounds of the present invention have a shifted chromophore able to absorb much more of the strongest emission wavelength from medium pressure mercury arc lamps at 365 nm.

Spectra were acquired at an equal weight percent concentration of 0.05 gdm$^{-3}$ in methanol using a Perkin Elmer Lambda 35 UV/VIS spectrophotometer.

The invention claimed is:
1. Compounds of formula (I):

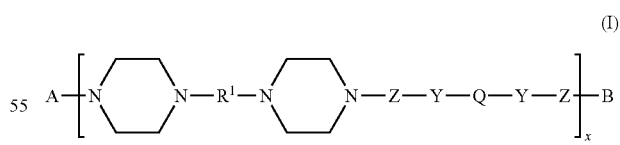

in which:
A represents a hydrogen atom, or a group of formula:

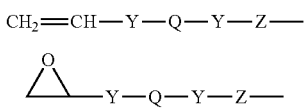

-continued

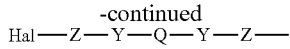

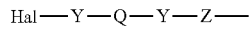

and B represents a halogen atom or a group of formula:

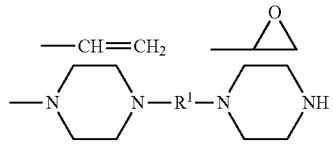

$R^1$ represents a group of formula (II) or (III):

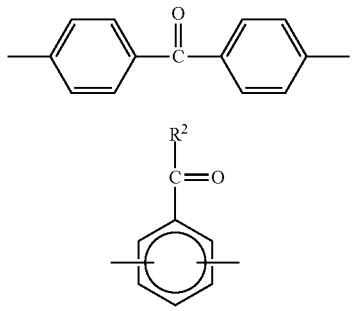

$R^2$ represents a $C_1$-$C_6$ alkyl group, an aryl group or a substituted aryl group having one or more $C_1$-$C_6$ alkyl, $C_1$-$C_6$ alkoxy or phenyl substituents;

Z represents a group of formula —$(CHR^3)_n$—, where $R^3$ represents a hydrogen atom, a hydroxy group or a $C_1$-$C_4$ alkyl group, and n is a number from 0 to 6;

Y represents a carbonyl group or a group of formula —$CH_2$—;

Q represents a residue of a $C_2$-$C_6$ polyalkylene glycol or is a bis($C_1$-$C_6$ hydroxyalkyl)ether;

Hal represents a halogen atom; and x is a number from 1 to 100.

2. Compounds according to claim 1, in which Hal represents a chlorine or bromine atom.

3. Compounds according to claim 1, in which Z represents a group of formula —$CHR^3$—.

4. Compounds according to claim 1, in which $R^3$ represents a hydrogen atom, a methyl group or an ethyl group.

5. Compounds according to claim 4, in which $R^3$ represents a hydrogen atom.

6. Compounds according to claim 1, in which Z represents a group of formula —$(CHR^3)_n$—, n is a number from 2 to 6 and one of $R^3$ represents a hydrogen atom or a $C_1$-$C_4$ alkyl group, and the other or others of $R^3$ represent hydrogen atoms.

7. Compounds according to claim 1, wherein Q represents a group of formula -D-Q'-D-, where:

D represents a group of formula —$[O(CHR^4CHR^5)a]y$—, —$[O(CH_2)_bCO]_y$— or —$[O(CH_2)_bCO]_{(y-1)}$—$[O(CHR^4CHR^5)_a]$—; where:

$R^4$ and $R^5$ independently represent a hydrogen atom or a $C_1$-$C_4$ alkyl group;

a is a number from 1 to 2;

b is a number from 4 to 5;

y is a number from 1 to 10; and

Q' represents a residue of dihydroxy compound.

8. Compounds according to claim 7, in which y is a number from 3 to 10.

9. Compounds according to claim 8, in which D represents a group of formula —$[O(CHR^4CHR^5)_a]_y$— where a is an integer from 1 to 2, and y is a number from 1 to 10.

10. Compounds according to claim 8, in which D represents a group of formula —$[OCH_2CH_2]_y$—, —$[OCH_2CH_2CH_2CH_2]_y$— or —$[OCH(CH_3)CH_2]_y$—, where y is a number from 1 to 10.

11. Compounds according to claim 8, in which D represents a group of formula —$[O(CH_2)_bCO]_y$—, where b is a number from 4 to 5 and y is a number from 1 to 10.

12. Compounds according to claim 8, in which D represents a group of formula —$[O(CH_2)bCO]_{(y-1)}$—$[O(CHR^4CHR^5)_a]$—, where a is a number from 1 to 2, b is a number from 4 to 5 and y is a number from 1 to 10.

13. Compounds according to claim 7, in which a is 2 and y is a number from 1 to 10.

14. Compounds according to claim 7, in which y is a number from 1 to 6.

15. Compounds according to claim 7, in which Q' is a residue of a poly $C_2$-$C_6$ alkylene glycol.

16. Compounds according to claim 7, in which Q' is a residue of ethylene glycol, propylene glycol, butylene glycol, 2,2-propanediol, polyethylene glycol, polypropylene glycol or polybutylene glycol.

17. Compounds according to claim 1, in which Q is a residue of a poly $C_2$-$C_6$ alkylene glycol.

18. Compounds according to claim 17, in which Q is a residue of ethylene glycol, propylene glycol, butylene glycol, 2,2-propanediol, polyethylene glycol, polypropylene glycol or polybutylene glycol.

19. Compounds according to claim 1, in which x is a number from 1 to 50.

20. The compound of formula (I) of claim 1 used as a photoinitiation sensitiser.

21. An energy-curable composition comprising: (a) a polymerisable monomer, prepolymer or oligomer; (b) a photoinitiator; and (c) the sensitiser of claim 20.

22. A process for preparing a cured polymeric composition by:
(a) applying to or printing onto a substrate an energy-curable composition according to claim 21; and
(b) exposing the energy-curable composition to actinic radiation.

23. A process according to claim 22, in which the actinic radiation is ultraviolet radiation.

* * * * *